(12) United States Patent
Head

(10) Patent No.: US 7,496,968 B2
(45) Date of Patent: Mar. 3, 2009

(54) ABSORBENT EYELID PROTECTOR AND METHOD

(76) Inventor: Cindy Head, 16569 N. 91st Dr., Peoria, AZ (US) 85382

( * ) Notice: Subject to any disclaimer, the term of this patent is extended or adjusted under 35 U.S.C. 154(b) by 0 days.

(21) Appl. No.: 11/339,885

(22) Filed: Jan. 26, 2006

(65) Prior Publication Data
US 2007/0169245 A1 Jul. 26, 2007

(51) Int. Cl.
*A61F 9/00* (2006.01)
(52) U.S. Cl. .......................................... 2/15; 2/11; 2/12
(58) Field of Classification Search ....................... 2/15, 2/11, 12
See application file for complete search history.

(56) References Cited
U.S. PATENT DOCUMENTS
2,165,668 A * 7/1939 Vaccaro ............................ 2/15

2,389,223 A * 11/1945 Werner .............................. 2/15
2,527,947 A * 10/1950 Loos ............................ 604/294
2,572,638 A * 10/1951 Loos ............................ 128/858
4,979,811 A * 12/1990 Boyer ............................ 351/44
4,995,114 A * 2/1991 Price, Jr. ............................ 2/15
5,191,897 A * 3/1993 Meshel ........................ 600/558
5,740,550 A * 4/1998 Yavitz .............................. 2/15
6,623,517 B1 * 9/2003 DeLuisa et al. .............. 607/109

* cited by examiner

*Primary Examiner*—Gary L Welch
*Assistant Examiner*—Richale L Quinn
(74) *Attorney, Agent, or Firm*—Craig Weiss; Jeffrey Weiss; Weiss & Moy, P.C.

(57) ABSTRACT

An absorbent eyelid protector device having a substantially absorbent interior portion, adapted to fit over a closed eyelid of the wearer. The interior portion may be soaked in a liquid to help cool the eye of a wearer. A substantially water-impervious exterior portion can be provided, and may be used for advertising by placing names, logos, or the like thereon.

3 Claims, 1 Drawing Sheet

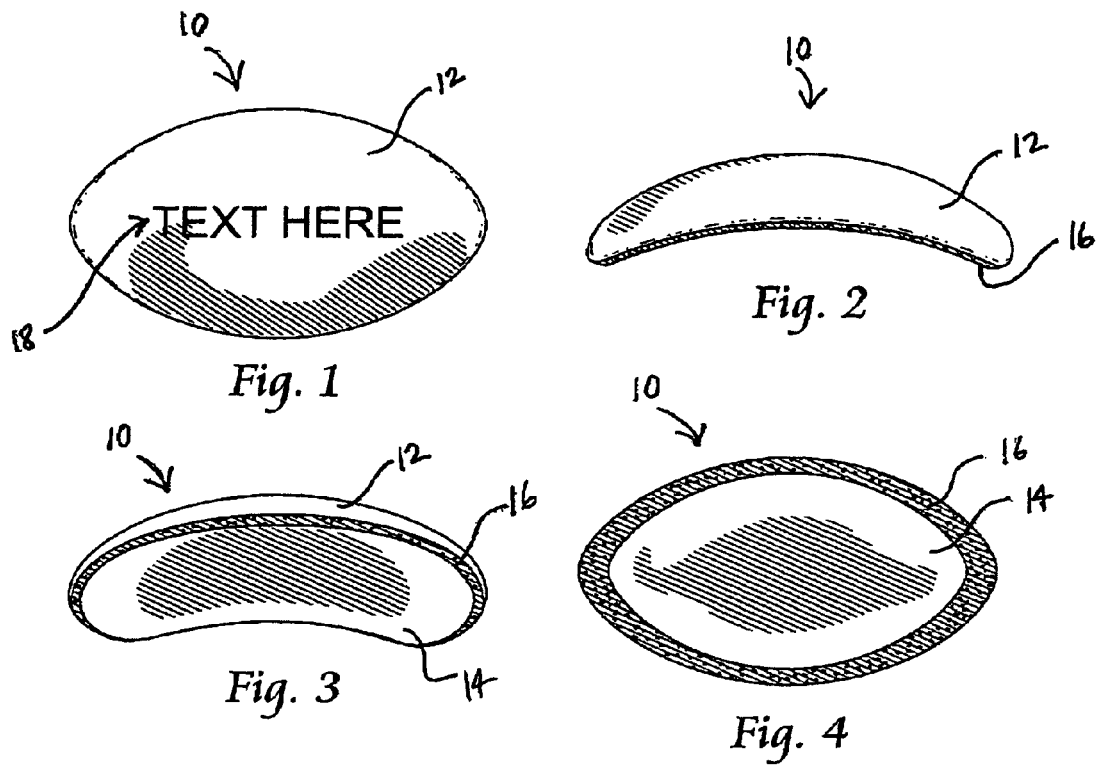
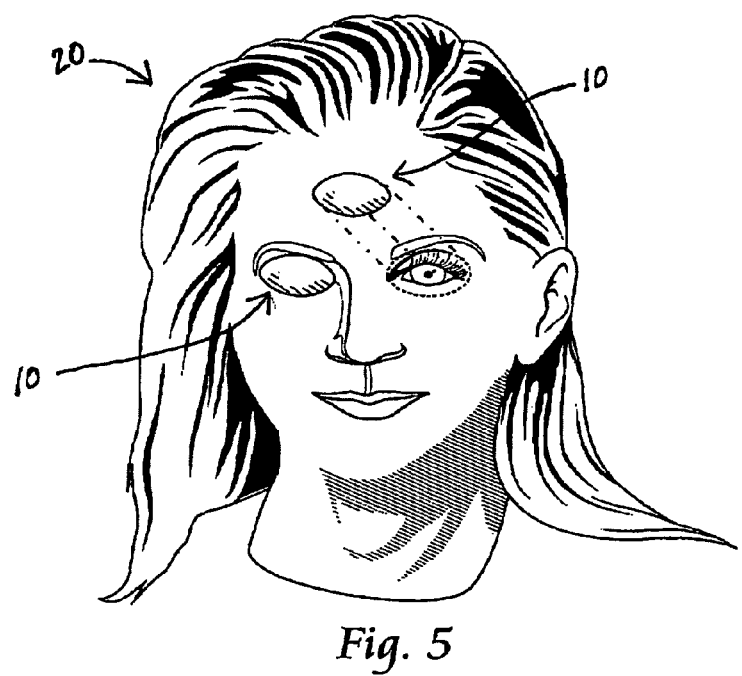

ABSORBENT EYELID PROTECTOR AND METHOD

FIELD OF THE INVENTION

This invention relates generally to protective coverings for human eyelids and, more particular, to eyelid protectors that provide protection from the sun and that may be absorbent and feel cool on the eyelids when in position on a wearer and/or that may convey an advertised message.

BACKGROUND OF THE INVENTION

Eyelid protector devices are commonly used by sunbathers to protect the wearer's eyes from the sun while sunbathing. In the prior art, there are examples of eyelid protector devices that have been created for such purposes. Such eyelid protector devices are often made of plastic or some other material that can become heated by the sun. A disadvantage exists with such eyelid protector devices in that they can become hot to the touch while the wearer is sunbathing, in turn becoming uncomfortable to the wearer. In other prior art eyelid protector devices, the individual eyepieces are often connected by a bridge that covers the bridge of the nose of the wearer, and/or have a headband, straps, bows or the like to keep them in place on the head of the wearer. A disadvantage exists with such eyelid protector devices as well, in that the bridge, headband, straps, and bows block the sun, thereby preventing the skin underneath from tanning. As a result, the wearer will often have undesired tan lines across his or her nose and sides of the face after sunbathing.

A need therefore exists for an eyelid protector device that feels cool on the eyelids of a wearer and that stays in place without leaving undesired tan lines across the nose and sides of the face of the wearer.

The present invention satisfies these needs and provides other, related advantages.

SUMMARY OF THE INVENTION

In accordance with an embodiment of the present invention, an absorbent eyelid protector device is disclosed. The device comprises: a substantially absorbent interior portion having a convex outer surface and a concave inner surface; wherein the inner surface of the interior portion is contoured to fit over the closed eyelid of a wearer.

In accordance with another embodiment of the present invention, an absorbent eyelid protector device is disclosed. The device comprises: a substantially water-impervious exterior portion having a convex outer surface and a concave inner surface; and a substantially absorbent interior portion having a convex outer surface and a concave inner surface; wherein the convex outer surface of the interior portion is proximate the concave inner surface of the exterior portion; wherein the inner surface of the interior portion is contoured to fit over the closed eyelid of a wearer.

In accordance with a further embodiment of the present invention, a method for protecting eyelids from the sun is disclosed. The method comprises: providing an absorbent eyelid protector comprising: a substantially absorbent interior portion having a convex outer surface and a concave inner surface, wherein the inner surface of the interior portion is contoured to fit over the closed eyelid of a wearer; soaking the absorbent eyelid protector in a liquid; placing the absorbent eyelid protector over a closed eyelid; and sunbathing with the absorbent eyelid protector in position.

BRIEF DESCRIPTION OF THE DRAWINGS

FIG. 1 is a front view of an absorbent eyelid protector device, consistent with an embodiment of the present invention.

FIG. 2 is a top, perspective view of the absorbent eyelid protector device of FIG. 1.

FIG. 3 is a bottom, perspective view of the absorbent eyelid protector device of FIG. 1.

FIG. 4 is a back view of the absorbent eyelid protector device of FIG. 1.

FIG. 5 is a front view of a pair of absorbent eyelid protector devices, consistent with an embodiment of the present invention.

DETAILED DESCRIPTION OF THE PREFERRED EMBODIMENTS

An embodiment of an absorbent eyelid protector device 10 consistent with an embodiment of the present invention is shown in FIGS. 1-5. Referring first to FIG. 3, in one embodiment, the body of the absorbent eyelid protector device 10 may be a laminate consisting of two main layers: an exterior portion 12 having a convex outer surface and a concave inner surface and an interior portion 14 having a convex outer surface and a concave inner surface.

Referring to FIGS. 1-3 and 5, in this embodiment, the exterior portion 12 may be composed of a substantially water-impervious material, such as latex, rubber or foam. Referring to FIGS. 3 and 4, the interior portion 14 may be an absorbent material, such as a sponge-like material, terry cloth, foam or other type of fabric capable of absorption. In one embodiment, as best shown in FIGS. 3 and 4, it may be desired to provide a ridge 16 around the perimeter of the absorbent eyelid protector device 10.

As best seen in FIGS. 2, 3 and 5, the absorbent eyelid protector device 10 may be shaped to more reliably fit in position over the closed eyelid of a wearer 20.

It should be noted that it may be desired to provide an absorbent eyelid protector device 10 which is not a laminate, and which has only an interior portion 14 comprised of a substantially absorbent material, and having a convex outer surface and a concave inner surface. It may also be desired to provide an absorbent eyelid protector device 10 which is comprised of fabric containing an absorbing agent, and having a convex outer surface and a concave inner surface.

In one embodiment, as best seen in FIG. 1, the exterior portion 12 of the absorbent eyelid protector device 10 has space on which decoration and/or advertising 18, such as names, logos, rhinestones, or the like may be placed. Because the absorbent eyelid protector device is likely to be used in a public setting, such as a beach or a public pool, the exterior surface may provide an ideal advertising space. It should be noted that it may be desired to provide advertising 18 on a prior art eyelid protector device, and this is considered to be another embodiment of the present invention.

Statement of Operation

In order to prepare the absorbent eyelid protectors 10 so that they may be used to cool and protect the eyes of a wearer, a wearer would first soak the absorbent eyelid protectors 10 in liquid, typically water, drawing liquid into the interior portion 14. Once saturated, the wearer would then place the absorbent eyelid protectors 10 in position over his or her closed eyes, with the interior portion 14 contacting an outer surface of a user's eyelid. When the interior portion 14 becomes dry, the wearer would remove the absorbent eyelid protector 10 from his or her eyes and repeat the preparation process if further cooling and protection of the eyes is desired.

While the invention has been particularly shown and described with reference to the preferred embodiments thereof, it will be understood by those skilled in the art that the foregoing and other changes in form and details may be made therein without departing from the spirit and scope of the invention.

I claim:

1. A method for protecting eyelids from the sun comprising:
    providing an absorbent eyelid protector comprising:
    a substantially absorbent interior portion having a convex outer surface and a concave inner surface;
    wherein the inner surface of the interior portion is contoured to fit over the closed eyelid of a wearer; and
    an exterior portion having a convex outer surface and a concave inner surface wherein the convex outer surface and the concave inner surface each comprises a substantially water impervious material and wherein the convex outer surface of the interior portion is proximate the concave inner surface of the exterior portion;
    wherein the exterior portion is comprised of at least one of latex and rubber;
    wherein an outer surface of the water-impervious exterior portion is exposed;
    advertising text located on the exposed outer surface of the water-impervious exterior portion;
    soaking the absorbent eyelid protector in a liquid;
    placing the absorbent eyelid protector over a closed eyelid; and
    sunbathing with the absorbent eyelid protector in position.

2. The method of claim 1 wherein the interior portion is comprised of one of a sponge-like material, terry cloth and foam.

3. The method of claim 1, wherein the absorbent eyelid protector further comprises a ridge around a perimeter of the interior portion.

* * * * *